United States Patent [19]

Macovski

[11] 3,950,613
[45] Apr. 13, 1976

[54] X-RAY ENCODING AND DECODING SYSTEM

[76] Inventor: Albert Macovski, 4100 Mackay Drive, Palo Alto, Calif. 94306

[22] Filed: Dec. 26, 1973

[21] Appl. No.: 428,453

[52] U.S. Cl. ............ 178/6.8; 178/DIG. 5; 250/274; 350/162 SF
[51] Int. Cl.². H04N 3/00; G01N 23/20; G02B 5/18
[58] Field of Search........... 178/DIG. 5, DIG. 1, 6.8, 178/DIG. 27; 250/505, 510, 272, 273, 274, 320, 494, 321, 496, 237 G, 226, 363, 366, 369; 313/59; 350/162 SF, 162 ZP; 358/53, 55, 81, 82

[56] References Cited
UNITED STATES PATENTS

| | | | |
|---|---|---|---|
| 3,229,089 | 1/1966 | Sasao | 178/DIG. 5 |
| 3,766,383 | 10/1973 | Harris et al. | 250/272 |
| 3,801,785 | 4/1974 | Barrett | 250/320 |
| 3,829,688 | 8/1974 | Barrett | 250/272 |

*Primary Examiner*—Robert L. Griffin
*Assistant Examiner*—R. John Godfrey

[57] ABSTRACT

An x-ray beam is transmitted through an object under study and through an encoding grating structure consisting of alternate stripes of materials each having different x-ray absorption characteristics. The recorded image has a grating structure which is modulated by the energy spectrum information represented by the difference of the absorption characteristics of the two stripe materials. The grating amplitude information is decoded by coherent optical filtering or by scanning and used to indicate the presence of specific materials in the object.

20 Claims, 7 Drawing Figures

X-RAY ENCODING AND DECODING SYSTEM

BACKGROUND OF THE INVENTION

1. Field of the Invention

This invention relates to x-ray imaging systems. In a primary application the invention relates to obtaining images representing specific materials in the body.

2. Description of Prior Art

Present x-ray imaging systems record the transmission of objects, such as body tissue, to a broad energy spectrum. This spectrum is generated by the "bremstrahlung" or braking radiations caused by an electron beam when it strikes a metallic target. This broad energy spectrum does not allow the radiologist to distinguish between various materials. Thus the total information in a conventional radiograph is due to nonselective absorption of materials.

It would be highly desirable to be capable of deriving information indicating specific regions of the x-ray spectrum. These could be used to form images representing specific materials of the body.

Unfortunately, band-pass filters which transmit specific regions of the x-ray spectrum do not exist. Only relatively subtle filtering can be accomplished in the x-ray region because of the nature of the absorption characteristics of materials.

There have been a number of earlier, relatively impractical efforts at delineating selective energy spectrum information using x-rays. These include B. Jacobson and R.S. Mackay, "Advances in Biological and Medical Physics," Academic Press, Vol. VI, (1958); R.S. Mackay, IRE Transactions on Medical Electronics, Vol. ME 7, p. 77 (1960); and B. Jacobson, American Journal of Roent., Vol. 91, p. 202 (1964). These have involved the use of mechanically scanned, monochromatic x-ray sources to obtain transmission information at specific wavelengths. Mechanical analog computers were used to find the thicknesses of the various body materials at each point by moving wedge shaped structures into the x-ray beam until the required output was obtained. Many of these studies produced interesting diagnostic results including images of specific body materials including bone, soft tissue and the natural iodine in the thyroid. However, the limitations of the relatively low energy monochromatic sources, the relatively slow mechanical scanning and the low resolution of the resultant images made these systems unsuitable for clinical diagnostic radiology.

The use of gratings to encode spectral information is well-known in the visible spectrum. Here the principle incentive is to avoid the registration problem that would otherwise ensue using three separate films or television cameras for the red, green and blue images. The problem is not, as in the x-ray spectrum, the availability of suitable spectral filters for the various spectral components.

Some examples of such encoding and decoding systems for color renditions in the visible spectrum are illustrated in U.S. Pat. No. 2,050,417 granted to C. Bocca, U.S. Pat. No. 3,504,606 granted to A. Macovski and U.S. Pat. No. 3,378,633 granted to A. Macovski.

SUMMARY OF THE INVENTION

An object of this invention is to provide apparatus for obtaining images representing the transmission at specific x-ray energy regions. It is a further object of this invention to provide apparatus for obtaining images representing the amount of specific materials within an object being studied. In a primary application of this invention in diagnostic radiology, separate images are obtained indicating the thicknesses of bone, soft tissue, and administered contrast material.

Briefly, in accordance with the invention, a grating structure is introduced into the x-ray path so as to create a modulated grating image at the recording plane. The alternate stripes of the grating have specific x-ray energy spectrum transmission characteristics so that the modulated grating image has an energy spectrum characteristic equal to the difference of the individual spectra of the alternate stripes. The grating pattern is decoded by coherent optical filtering or by scanning the recorded pattern followed by electrical filtering. A number of grating structures at different angles and different periodicities can be used simultaneously with each grating representing a different x-ray encoding spectrum. The decoded grating images, each representing a different portion of the x-ray spectrum, are used to delineate specific materials within the object under study.

BRIEF DESCRIPTION OF THE DRAWINGS

For a more complete disclosure of the invention, reference may be made to the following description of several illustrative embodiments thereof which is given in conjunction with the accompanying drawing, of which.

Figure 1:
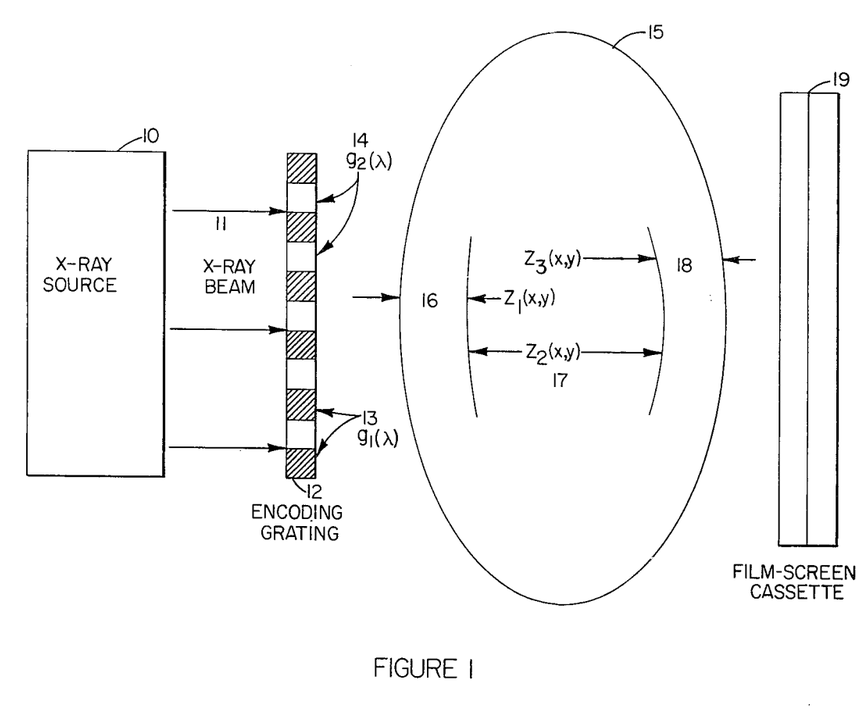
FIG. 1 is a cross-sectional view of an encoding embodiment of the invention.

An understanding of the broad aspects of the invention may best be had by reference to FIG. 1. Here an x-ray source 10 is used to create an x-ray beam 11 in a conventional manner by allowing a high energy electron beam to strike a metallic target and create substantially a point source of x-rays. The energy spectrum in this beam is the conventional "bremstrahling" or braking radiation which is a broad energy spectrum. The beam is passed through an encoding grating 12 which consists of alternate stripes 13 and 14 of differing materials. These materials each have specific x-ray energy spectral transmission characteristics. The spatially modulated x-ray beam is then passed through the object under study 15 which, in diagnostic radiology, would be the human body. The object is shown, for illustrative purposes, to be composed of regions containing different materials. For example region 16, having thickness $z_1$ can consist of bone; region 17, having thickness $z_2$ can consist of soft tissue; with region 18, having thickness $z_3$, consisting of a blood vessel containing iodine. The x-ray beam emerging from the body is recorded using a conventional film-screen cassette 19. These cassettes normally consist of a double emulsion photographic film with a scintillation phosphor layer on either side. The x-ray photons give up most of their energy to the flourescent screen. The resultant light exposes the film.

The developed film contains a standard image in addition to a modulated high frequency structure. The standard image is relatively unmodified by the encoding grating 12 other than having the spectral content of the x-ray beam modified by the average transmission of the two stripes. The high-frequency grating structure on the film is amplitude modulated by the spectral information represented by the difference in transmission of the two gratings. Thus, if the spectral transmission of stripe 13 is $g_1(\lambda)$ and of stripe 14 is $g_2(\lambda)$, the transmission $\tau$ of the grating structure is given by $$\tau = \frac{1}{2}\left[(g_1(\lambda) + g_2(\lambda)) + (g_1(\lambda) - g_2(\lambda))\cos\omega x\right]$$

where $\omega$ refers to the spatial angular frequency of the grating. In the above equation, for methematical convenience, the grating is assumed to have a sinusoidal transmission. The equation shows the average transmission spectra, which is equal to the sum of the two stripe spectra, plus the modulated grating signal which is determined by the difference of the two spectra. This difference spectrum, $g_1-g_2$, can be chosen to provide a wide variety of characteristics which would otherwise by physically unrealizable. The difference spectrum can thus be used to indicate the presence of specific materials, or to eliminate and thus "see through" other materials.

Figure 2A:
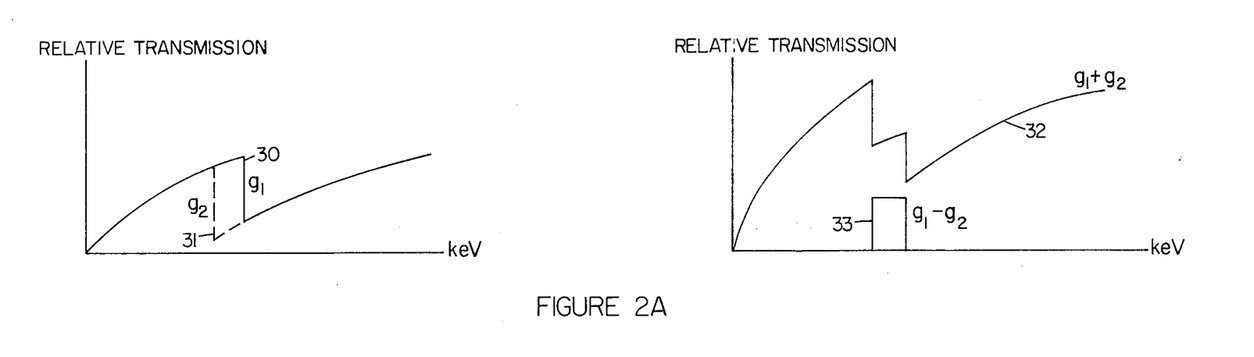
FIG. 2a is a graph illustrating a representative encoding energy spectrum.

FIGS. 2a and 2b illustrate some representative spectra. In FIG. 2a two materials of similar atomic numbers are used as the stripe materials so that their K absorption regions will be relatively close. Their thicknesses are chosen so that their transmission characteristics 30 and 31 tend to match at the high and low energy regions. Thus they essentially differ only in the vicinity of their K absorption edges. Their sum spectrum 32 will only slightly modify the conventional broad x-ray spectrum so that the resultant radiograph will be essentially unmodified when viewed by the naked eye. The high frequency grating structure on the radiograph, however, will be modulated by the $g_1-g_2$ spectrum 33. As shown, this can be made to approximate a bandpass type filter anywhere within the x-ray spectrum by an appropriate choice of materials. A filter of this type, directly filtering the x-ray beam, is physically unrealizable. As an example, the $g_1$ and $g_2$ materials can be chosen as neodymium and iodine. These will create a band-pass filter in the region of the iodine absorption edge. The encoded image information which modulates the high frequency grating structure will thus be dominated by the iodine absorption and therefore strongly indicate the presence of iodine in the body. When this modulated image is decoded it will be very useful for contrast studies of the circulation system when iodine contrast material is administered.

Figure 2B:
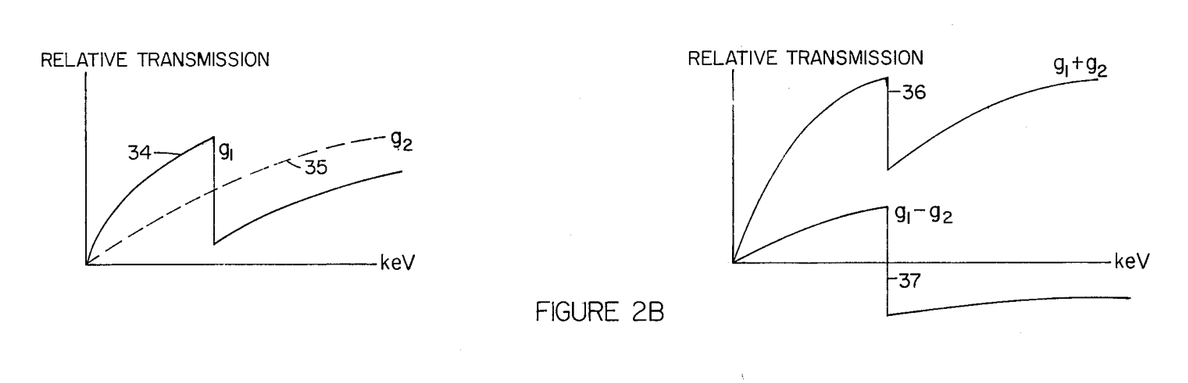
FIG. 2b is a graph illustrating another example of a representative encoding energy spectrum.

FIG. 2b further indicates the versatility of the spectra available as the grating modulation information. Here $g_1$ is a material having a K absorption edge within its spectrum 34. The $g_2$ material has a relatively low atomic number, such as aluminum, and thus has the continuous spectrum 35 since its K edge is so low as to be undiscernable. Again, the sum spectrum 36 is relatively non-specific. The difference spectrum 37 has the interesting property of being partially negative. This property is, of course, physically impossible in any direct filtering operation. A spectrum of this type can be designed to allow a radiologist to "look through" certain body materials such as soft tissue or bone. The spectrum is designed to provide a zero integrated output when projected through certain specific materials. For example, assume that it is desired to see through a bone structure having a spectral transmission $b(\lambda)$. The materials $g_1$ and $g_2$ are chosen so as to provide the relationship $$\int [g_1(\lambda) - g_2(\lambda)] b(\lambda) d\lambda = 0$$

Thus the modulated grating signal, when decoded, will not show this bone structure. It will show the remainder of the tissue since its spectrum will not, in general, provide a zero output.

Although a single grating structure is shown in FIG. 1, a number of gratings can be used simultaneously. These can all be in the same plane with the grating stripes having different spatial frequencies. This implies different angles or periodicities since spatial frequency is a two-dimensional vector. Thus each grating signal would be at a different two-dimensional spatial frequency so that they can be individually separated in the decoding process. Each grating would have a different set of stripes to encode a different spectral response to provide the isolation of a selected material.

Figure 3:
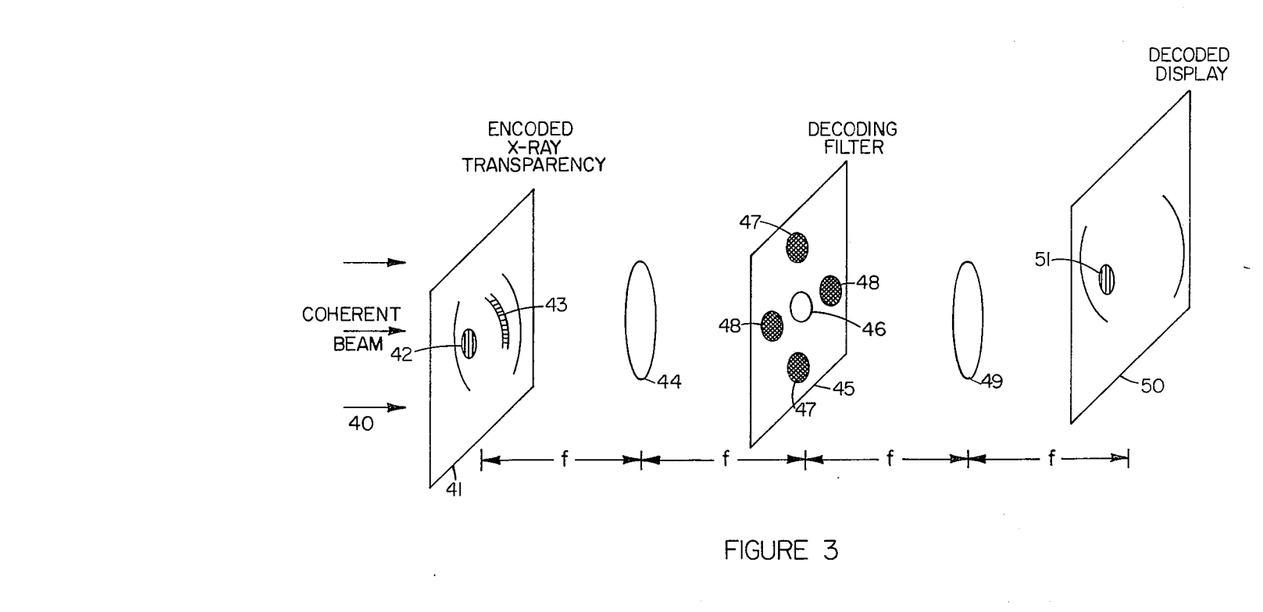
FIG. 3 is an illustration of an optical decoding embodiment of the invention.

Once the desired spectral information is encoded as amplitude modulation of grating signals on a film recording, the decoding can be accomplished in a number of well-known ways. One method is the coherent optical decoding system shown in FIG. 3. This is identical to those described in U.S. Pat. No. 3,504,606 granted to A. Macovski and U.S. Pat. No. 2,050,417 granted to C. Bocca. A plane-wave source 40 of coherent light is used which is usually derived using a point source of light and a collimating lens. The transparency 41 is the encoded x-ray recording. As an example, structure 42 is shown with vertical stripes and structure 43 with horizontal stripes. These have resulted from encoding gratings of the type shown in FIG. 1 whose x-ray encoding spectra have interacted with the materials of structure 42 and 43 to produce these grating patterns. The front and back focal planes of lens 44 form a Fourier transform relationship so that plane 45 contains a two-dimensional Fourier transform of encoded transparency 41. Thus structure 42 with vertical lines appears in the dots 48 and structure 43 with the horizontal lines appears in the dots 47. The conventional low-frequency pattern appears in the undiffracted region or the central dot 46. Any combination of these dots can be blocked, with the subsequent Fourier transform provided by lens 49, producing the processed image 50. In the example shown, only one or both of the dots 48 are opened so as to show the decoded structure 51 which was originally represented by vertical lines. Rather than observing the decoded structures individually in sequence, different color filter material can be placed over the openings corresponding to the various dot pairs. Thus the various structures will be decoded as having different colors so that all of the spectral information will be simultaneously available.

Figure 4:
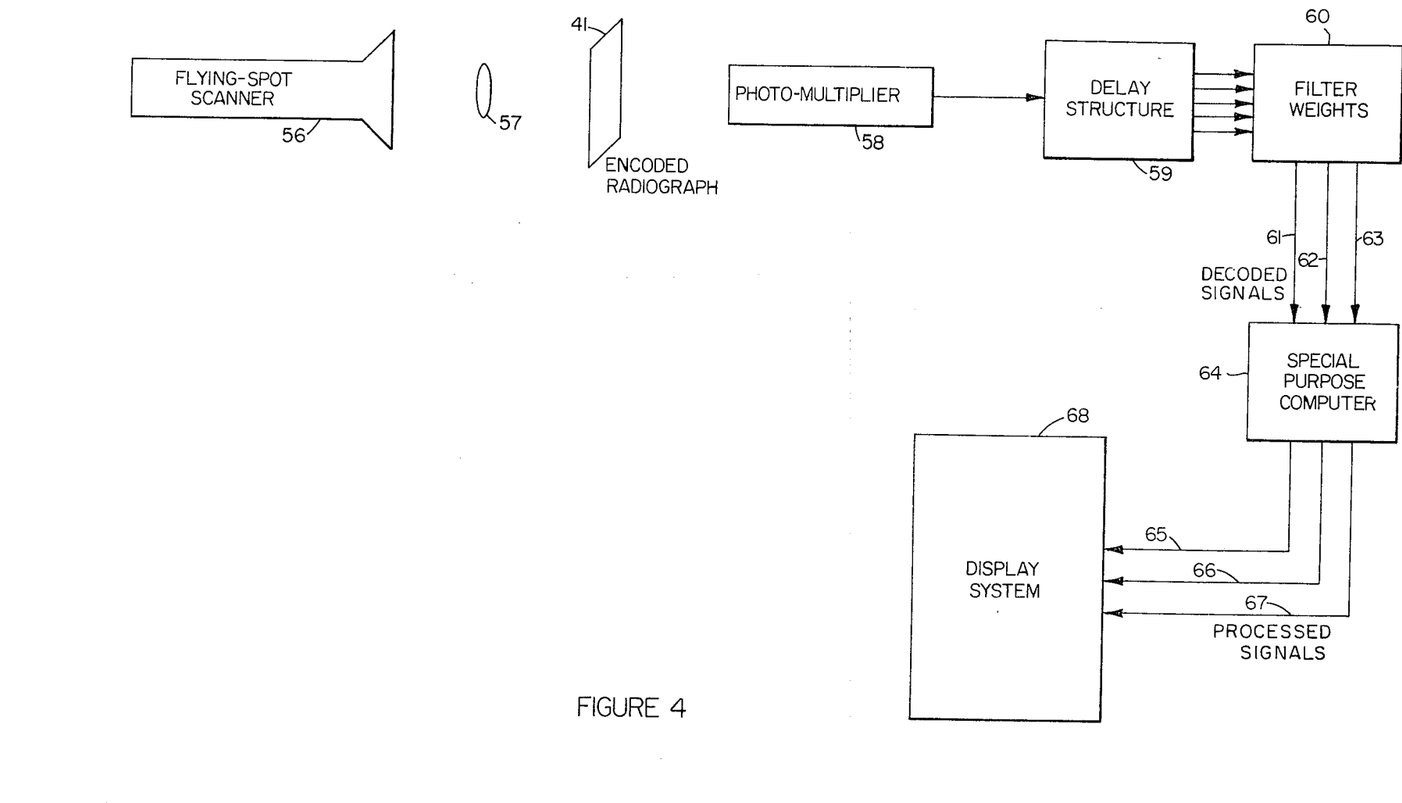
FIG. 4 is a block diagram of a scanned decoding embodiment of the invention.

One of the problems with the optical decoding system is its lack of flexibility. For example, although each spectrally encoded x-ray region is indicative of specific materials, these decoded spectral signals do not directly represent specific materials without subsequent processing. It would thus be desirable to obtain electrical signals which represent the various encoded x-ray spectra to allow for further processing. These can then be combined in a computer to produce images representing specific materials. A method of obtaining these electrical signals is shown in FIG. 4. Here a Flying-Spot Scanner 56 is imaged, using lens 57, onto the encoded radiograph 41. The resultant scanned signal is derived using photo-multiplier 58. A two-dimensional filtering system can be used to extract the individual spatial frequency carriers which represent the various encoding gratings. A filtering system of this type is described in the publication "Encoding and Decoding of Color Information Using Two-Dimensional Spectral Filtering," by L. F. Schaefer and A. Macovski in the July 1972 issue of IEE Transactions on Computers, Vo. C-21, No. 7. In the filtering operation an array of delay elements 59 is used so as to simultaneously make available a matrix of points. Various weighted sums of these delayed signals are taken in 60. Each weighted sum represents a filtered region in the two-dimensional frequency spectrum of the image. The outputs of each weighted sum 61, 62 and 63 thus represent specific grating signals and thus specific regions of the x-ray spectrum. These are combined in special purpose computer 64 to form processed signals 65, 66 and 67 which represent the presence of specific materials. These signals are applied to display system 68 where they can be displayed simultaneously, sequentially, or stored for future use. These signals might, for example, represent the bone, soft tissue, and administered contrast material images in the body which could be displayed individually or in combination using, for example, a color monitor.

It is often required, for signal to noise considerations, to use relatively narrow band filters on the various grating signals to properly extract them. These filters result in reduced resolution images. This problem can be overcome to some extent by using the low frequency or average image to provide the detail information. One method of utilizing this signal is similar to that used in color television where the luminance signal provides the high frequency information. Thus the filtered high frequency information from the average or conventional image is added to each of the material signals 65, 66 and 67 in either individual displays or a combined color display. Alternatively a material signal at a particular color can be added to the average image. For example, an encoding grating can be designed to isolate some administered contrast material. A narrow band decoding filter is used to obtain a low-resolution high-sensitivity signal representing the presence of this material. This signal can be displayed in some color superimposed on a black and white conventional radiograph image. Thus the selective takeup of the contrast material will be clearly evident on a high resolution image representing the anatomy.

The computer 64 is the type described in a patent application entitled "X-Ray Imaging System" by the same inventor on June 25, 1973. The Ser. No. is 373,465 now U.S. Pat. No. 3,848,130 and the group number is 234. Referring to FIG. 1, the desired output images would directly indicate the thicknesses of the three different materials, $z_1(x,y)$, $z_2(x,y)$ and $z_3(x,y)$. Although the individual energy spectrum output signals 61, 62 and 63 in FIG. 4 can be designed to closely approximate the desired thickness signals 65, 66 and 67, in general computer 64 is required to generate the exact thickness signals from the energy spectrum signals. The attenuation of a specific material at a specific energy or wavelength is given by exp-$kz$, where $k$ is the absorption coefficient at the wavelength and $z$ is the thickness of the material. In general $k$ is a function of x-ray wavelength. The information recorded when broad-band x-rays are transmitted through three materials, as in FIG. 1, is given by $$I_a = \int a(\lambda)s(\lambda)\exp-[k_1(\lambda)z_1+ k_2(\lambda)z_2+ k_3(\lambda)z_3]d\lambda$$

where $s(\lambda)$ is the energy spectrum of the source and $k_1(\lambda)$, $k_2(\lambda)$ and $k_3(\lambda)$ are the absorption coefficients at the various wavelengths. The particular encoding spectrum used is given by $a(\lambda)$ which can represent a particular $g_1(\lambda) - g_2(\lambda)$ of a specific grating. To solve for the $z_1$, $z_2$ and $z_3$ values over the entire image a total of three equations are required. Thus, in addition to the equation shown, a $b(\lambda)$ and $c(\lambda)$ encoding spectrum must be used providing $I_b$ and $I_c$. The resultant measured $I_a$, $I_b$ and $I_c$ values 61, 62 and 63 are applied to computer 64 for the solution of the integral equation as described in application Ser. No. 373,465, now U.S. Pat. No. 3,848,130. The computer finds the $z$ values an every $x,y$ point in the image and thus provides the direct material output signals 65, 66 and 67. One of the three encoding spectra $a(\lambda)$, $b(\lambda)$ and $c(\lambda)$ can be supplied by the average transmission with the other two supplied by specific grating configurations. For more flexibility, however, they can all three be supplied by gratings at different angles or periodicities.

Two practical difficulties of the system of FIG. 1 relate to the grating 12. Firstly, a relatively high frequency structure of this type is difficult and expensive to construct. Secondly, using a finite x-ray source size, the penumbra affect will usually obliterate any high frequency structure which is separated from the film-screen cassette 19 by any appreciable distance. If the grating 12 is made coarse enough to be resolved by the x-ray source it will form an annoying interference pattern on the conventional radiograph image.

Figure 5:
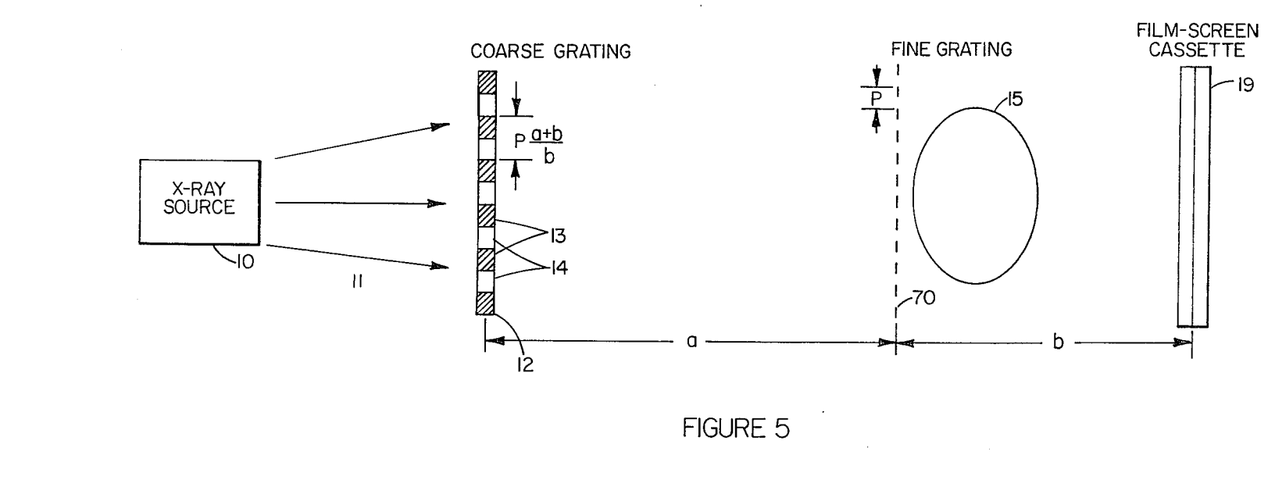
FIG. 5 is a cross-sectional view of another encoding embodiment of the invention.

These problems are solved by the system illustrated in FIG. 5. Here the desired grating image is derived using a combination of a coarse grating 12 and a grid or fine grating 70. These are in a collinating relationship so that a grating image is present at 19 only when both gratings are present. This grating image is independent of the size of the x-ray source. The collinating relationship requires that the product of the fine grating frequency and its distance from the film equals the product of the coarse grating frequency and its distance from the film. This is shown in FIG. 5 where the frequency or periodicity of the grid or fine grating is 1/P and that of the coarse grating is $$\left(\frac{b}{a+b}\right) 1/P.$$

This collinating relationship has been used in visible spectrum encoding systems. For example, a system of this type is described in U.S. Pat. No. 3,619,489, "Shadowing System For Color Encoding Cameras," granted to H. F. Frohbach, A. Macovski, and P. J. Rice on Nov. 9, 1971.

Only one of the two gratings need have the spectral encoding properties. As shown in FIG. 5, the spectral encoding stripes 13 and 14 are used only on coarse grating 12. Fine grating 70 is a relatively simple grating composed of alternate opaque and transparent regions.

Since it consists of only one material it can be constructed rather simply using tungsten wire or by sawing slots in a lead sheet. The coarse grating, which has specific thicknesses of different materials, is made relatively simply since it includes only a few cycles of a relatively coarse structure.

FIG. 5 shows both grating structures between the x-ray source and the subject since that arrangement provides the minimum amount of radiation to the body. This could result in some difficulty in resolving the fine grating because of the scatter processes within the subject. The effect of the scatter can be minimized by placing the grid 70 between the subject 15 and the film-screen cassette 19. Since the transmission of the fine grating is about 50%, this will only moderately increase the radiation to the subject. The coarse grating 12, which has greater attenuation, remains between the source and the subject to minimize the radiation to the subject. Moving the fine grating 70 closer to the film reduces the dimension b which has the added attribute of further reducing the periodicity of the coarse grating and thus making it easier to construct.

Figure 6:
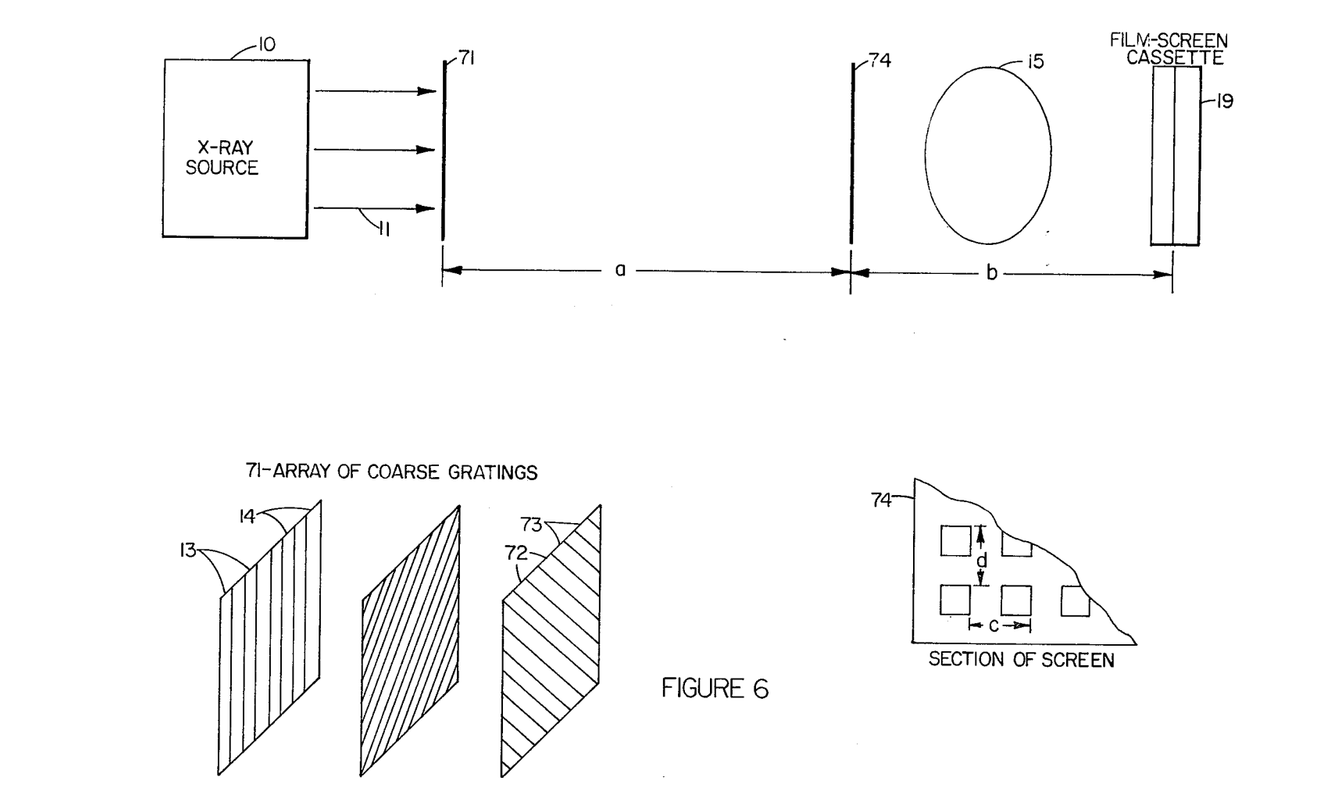
FIG. 6 is a cross-sectional view of a multiple-grating encoding embodiment of the invention.

As was previously discussed, a number of encoding gratings can be used simultaneously at different angles and/or periodicities to encode different x-ray spectra. FIG. 6 illustrates a multiple grating system using the same basic two-grating system as in FIG. 5. The coarse grating array 71 contains the encoding stripes having selective x-ray transmission characteristics. It is a sandwich of individual gratings. For example sets of alternate stripes 13 and 14 form a vertical grating, while stripe sets 72 and 73 form a diagonal grating. The fine screen structure 74 is essentially a number of grids sandwiched together each having a collinating relationship with one of the encoding coarse gratings. A number of grids or fine gratings form a screen having periodic apertures. This screen can be viewed as having a variety of periodicities in different directions which can form collinating relationships with the corresponding components in the coarse grating. For example, assume that the vertical encoding grating in the coarse grating array 71 has a spectral frequency $f_v$. Since the corresponding vertical grating in the screen 74 has a spatial frequency $1/c$, the required collinating relationship is given by $$\frac{b}{c} = (a+b)f_v$$

Similarly the screen 74 has a horizontal grating component $1/d$ and two diagonal components in opposite directions each having periodicities $(\sqrt{c^2+d^2})^{-1}$.

In both the arrangements of FIG. 5 and FIG. 6 harmonics of the coarse and fine grating structures, in addition to the fundamental frequencies, can be used to provide the collimating relationship. Thus, referring to FIG. 5, an appropriate relationship is given by $$n\frac{b}{c} = (a+b)f_v$$

where $n$ represents the harmonic number. The grating waveform, when expanded in a Fourier series, must have a significant component at the harmonic used. The use of harmonics has the advantage that lower frequency grating structures are used which should be easier to construct.

In the systems discussed thusfar the encoding operation was accomplished in a single x-ray exposure. If multiple exposures are used with mechanical motions between exposures some simplifications can result. Using the system of FIG. 5, a fine grating is used which has no specific spectral properties but simply has stripes of opaque material separated by transparent regions of equal width. The grating is arranged so that is can be translated by one-half period normal to the grating lines such that the opaque and transparent regions are interchanged. No coarse grating 12 is used. A filter material having the specific spectral transmission characteristics previously discussed is used to intercept the beam at any point. The filtered beam is transmitted solely through the transparent regions of the grating. After an exposure is made using the first filter material, the grating is translated by one-half period and a second exposure is made using a second filter material. The first and second filter materials can have the $g_1$ and $g_2$ characteristics shown in FIGS. 2a and 2b such as 30 and 31 or 34 and 35. The net result is identical to that obtained using an encoding grating, without the same construction problems. However, this procedure might be difficult in studying rapidly moving organs, such as the heart, where the two exposures would have to be accomplished quite rapidly. If a number of encoded gratings at different angles or periodicities are desired, they can be accomplished in sequence using two exposures for each grating image. The fine grating can either be changed or rotated between each pair of exposures so as to provide a new grating image.

If difficulty is experienced in resolving the grating image, due to source size problems, a dual grating system can again be used as in FIG. 5. The coarse grating, however, is also alternately opaque and transparent like the fine grating. Either one can be translated a half period between exposures.

In the methods previously discussed the various x-ray spectra were obtained by filtering of a broad-band x-ray source by some material having a prescribed transmission characteristic. An alternate general method of obtaining specific x-ray spectra is the use of relatively narrow-band x-ray emitters. The references previously cited in the Description of Prior Art by B. Jacobson and R. S. Mackay used monoenergetic sources. These, however were collimated into narrow beams for scanning one point at a time, thus providing a relatively long time for each image. If these monoenergetic sources are used over the entire image, using the grating techniques described, the image exposure time will be greatly reduced. Monoenergetic or narrow-band sources have the advantage of providing a high degree of selectivity to different materials.

One method of using these sources is the translated grating system previously described. Here, instead of using different filters for each exposure, a different narrow-band emitter is used. Thus a first monoenergetic source is used with the grating in one position and a second monoenergetic source is used with the grating in the second position. These sources can either be radioactive isotopes or fluorescent or secondary emitters. These secondary emitters are excited by a broad band x-ray source and emit narrow-band x-rays. A representative pair of monoenergetic sources are iodine and cerium secondary emitters whose wavelengths fall on either side of the absorption edge of the iodine absorption spectrum. Thus, the use of these two sources will form a grating pattern whose amplitude almost directly represents the amount of iodine present.

Monoenergetic sources can also be used in the single exposure systems illustrated in FIGS. 5, and 6. Here the stripes of different materials in the encoding gratings are replaced by stripes of different narrow-band emitters. Thus stripes 13 and 14 in FIGS. 5, and 6 can be radioactive isotopes radiating different x-ray wavelengths. In that case the source 10 would not be used. Alternatively stripes 13 and 14 can be fluorescent or secondary emitters. In that case a broad-band x-ray source is needed to excite their emission. This source should be positioned in such a way that the broad-band x-ray beam itself does not directly strike the object 15 but only strikes the secondary emitters. One method of accomplishing this is to have the x-ray beam strike the emitters at an angle as is done in the previously cited references by B. Jacobson and R. S. Mackay. In general, monoenergetic sources will provide greater material selectivity but require longer exposure times.

In the system of FIG. 6, coarse array 71 would include a number of emitting pairs of stripes which, as did the filters, would provide different encoded spectral information modulating the various grating images. The computer 64 in FIG. 4 is very simple in the case of monoenergetic sources since an algebraic equation is solved rather than an integral equation. The grating-pattern decoding systems using narrow-band x-ray emitters are identical to those using transmission filters. If monoenergetic emitters are used as the coarse gratings in FIGS. 5 and 6, the coarse grating, 12 or 71, becomes the effective source of the system. As such, its total size determines the ability to resolve structures within object 15. As with any x-ray system, the source size becomes more important for object planes further removed from the film-screen cassette 19. Thus the effective resolvable element size in an object plane is equal to the source size multiplied by the distance of the object plane to the film divided by the distance of the source to the film. Thus the size of an emitting coarse grating determines the system resolution and should be made comparable to the focal spot of x-ray tubes.

What is claimed is:

1. Apparatus for encoding x-ray energy spectral information from an object onto a recording surface compising a grating structure positioned in the x-ray beam path between an x-ray source and the recording surface, the grating structure containing alternate stripes of different materials, with each material having a different x-ray energy transmission spectrum whereby the difference of each of the products of the two grating material transmission spectra and the object transmission spectrum form an amplitude modulated grating image at the recording surface.

2. Apparatus as recited in claim 1 wherein the material of the first stripe includes a first element whose K absorption edge is within the x-ray spectrum emitted by the source and the material of the second stripe includes a second element having a higher atomic number than that of the first element.

3. Apparatus as recited in claim 1 wherein the transmission spectra of each of the two stripes provides substantially equal output at the recording surface when transmitted through a specific substance in the object whereby the recorded grating image does not include that substance.

4. Apparatus as recited in claim 1 including a grid structure located between the x-ray source and the recording surface containing an array of parallel stripes which are substantially opaque to the x-ray beam where the stripes are parallel to those of the grating and the product of the periodicity of the grid structure and its distance from the recording surface is equal to the product of the periodicity of the grating structure and its distance from the recording surface whereby a grating image is formed on the recording surface.

5. Apparatus as recited in claim 1 including one or more additional grating structures each having alternate stripes of different materials with each grating having a spatial frequency different from each other and different from that of the first grating.

6. Apparatus as recited in claim 5 including a screen located between the x-ray source and the recording surface having the equivalent spatial pattern of a composite of individual grid structures where the number of grid structures is equal to the number of grating structures and each grid structure contains an array of parallel stripes which are substantially opaque to the x-ray beam, where the stripes of each individual grid structure are parallel to a corresponding grating structure and the product of the periodicity of each grid structure and its distance from the recording surface is equal to the product of the periodicity of the corresponding grating and its distance from the recording surface.

7. Apparatus as recited in claim 6 where the composite of individual grid structure is an aperture screen which contains spatial frequency components corresponding to each of the individual grid structures.

8. Apparatus for decoding the spectral information which has been encoded onto a single recording using gratings having alternate stripes of different x-ray spectra comprising:
means for scanning the recording to provide a video signal consisting simultaneously of an average signal, which is the low frequency portion of the video signal, and one or more amplitude modulated grating signals each representing different energy spectra;
means for filtering the video signal to simultaneously provide separate filtered signals each representative of the average signal or one of the amplitude modulated grating signals; and
means for utilizing the filtered signals to provide an output image representative of specific materials in an object.

9. Apparatus as recited in claim 8 where the means for utilizing the filtered signals includes a computer for computing the amounts of each material present in the object.

10. Apparatus as recited in claim 8 where the means for utilizing the filtered signals includes means for simultaneously displaying the various materials in the object in different colors.

11. Apparatus as recited in claim 8 where the means for scanning the recording to provide a video signal includes a flying-spot scanner focused onto the recording and a photocell to measure the transmitted light.

12. Apparatus for encoding x-ray spectral information from an object onto a recording surface comprising:
an x-ray source wherein the x-rays are emitted from substantially a point source and form a diverging x-ray beam;

a grid structure of uniform spatial frequency positioned in the x-ray beam path between the x-ray source and the recording surface having substantially opaque and transparent alternate stripes;

means for translating the grid structure normal to the stripes so that the position of the opaque and transparent stripes are interchanged;

means for providing a first exposure with the grid structure in its first position and a second exposure with the grid structure in its translated position; and means for altering the spectrum of the x-ray source between the first and second exposures whereby the encoded recording is obtained consisting of an average component representing the sum of the x-ray spectra and an amplitude modulated grid pattern representing the difference of the x-ray spectra of the two exposures.

13. Apparatus as recited in claim 12 wherein the means for altering the spectrum of the x-ray source includes a first x-ray filter having a specific x-ray transmission spectrum which is placed in the x-ray beam path during the first exposure, and a second filter having an x-ray transmission spectrum different than the first filter which is placed in the x-ray beam path during the second exposure.

14. Apparatus as recited in claim 12 wherein the means for altering the spectrum of the x-ray source includes a first x-ray emitter which is used as the x-ray source for the first exposure and a second x-ray emitter which is used as the x-ray source for the second exposure.

15. Apparatus as recited in claim 14 wherein the first and second x-ray emitters are isotopic sources.

16. Apparatus as recited in claim 14 wherein the first and second x-ray emitters are secondary emitters excited by a broad-band x-ray source.

17. Apparatus as recited in claim 12 including an additional grating having substantially opaque and transparent alternate parallel stripes of uniform spatial frequency and placed within the x-ray beam in collimating relationship with the grid structure.

18. Apparatus for encoding x-ray spectral information from an object onto a recording surface comprising:

a grating structure containing alternate parallel stripes of x-ray emitting material each emitting a different energy spectrum whose emitted radiation passes through the object and strikes the recording surface; and a grid structure positioned between the grating structure and the recording surface containing an array of parallel stripes at a uniform spatial frequency which are substantially opaque to x-rays where the stripes are parallel to those of the grating and in collimating relationship to the grating.

19. Apparatus as recited in claim 18 wherein the first stripe of the grating is a radioactive isotope emitting an x-ray spectrum and the second stripe is a different radioactive isotope emitting a different x-ray spectrum.

20. Apparatus as recited in claim 18 wherein the first stripe of the grating is an x-ray secondary-emitting material and the second stripe is a different x-ray secondary-emitting material where the beam of a broadband source is used to excite the first and second stripes without substantially striking the object.

* * * * *